United States Patent [19]

Coates et al.

[11] Patent Number: 4,861,773

[45] Date of Patent: Aug. 29, 1989

[54] HETEROCYCLIC COMPOUNDS

[75] Inventors: William J. Coates, Welwyn Garden City; Lawrence I. Kruse, Tewin, both of England

[73] Assignee: Smith Kline & French Laboratories Limited, Welwyn Garden City, England

[21] Appl. No.: 149,743

[22] Filed: Jan. 29, 1988

Related U.S. Application Data

[63] Continuation-in-part of Ser. No. 41,819, Apr. 23, 1987, abandoned.

[30] Foreign Application Priority Data

Apr. 28, 1986 [GB] United Kingdom ............... 8610369
Oct. 24, 1987 [GB] United Kingdom ............... 8724962

[51] Int. Cl.$^4$ .................... A61K 31/54; C07D 417/04
[52] U.S. Cl. .................................. 514/222.8; 544/9; 548/341
[58] Field of Search ...................... 544/9; 514/222.8; 548/341

[56] References Cited

U.S. PATENT DOCUMENTS

| 3,464,988 | 9/1969 | Holava et al. | 260/250 |
| 4,423,045 | 12/1983 | Brown et al. | 424/246 |
| 4,489,074 | 12/1984 | Brown et al. | 424/246 |
| 4,602,019 | 7/1986 | Sircar et al. | 514/248 |
| 4,616,013 | 10/1986 | Coates | 514/222 |
| 4,692,447 | 9/1987 | Cignarella et al. | 514/248 |
| 4,755,511 | 7/1988 | Warrington | 514/248 |

FOREIGN PATENT DOCUMENTS

| 0052442 | 5/1982 | European Pat. Off. . |
| 0124314 | 11/1984 | European Pat. Off. . |
| 0145236 | 6/1985 | European Pat. Off. . |
| 0169443 | 1/1986 | European Pat. Off. . |
| 0181145 | 5/1986 | European Pat. Off. . |
| 1292645 | 4/1969 | Fed. Rep. of Germany . |
| 2185977 | 8/1987 | United Kingdom . |
| 8601506 | 3/1986 | World Int. Prop. O. . |

OTHER PUBLICATIONS

Holava et al., J. Med. Chem., 14, 3, 262-4 (1971).
Yamada et al., J. Med. Chem., 25, 975-982 (1982).
Mukherje et al., J. Ind. Chem. Soc., 58, 1023-4 (1981).
Cignarella et al., El Farmaco, 33, 866-74 (1978).
Ege et al., Justus Liebigs Ann. Chem., 5, 791-9 (1977).
Ege et al., Liebigs Ann. Chem., 5, 656-74 (1979).
Cignarella et al., Il Farmaco, 37, 133-44 (1982).
Loriga et al., Il Farmaco, 34, 72-80 (1978).
Curran et al., J. Med. Chem., 17, 3, 273-80 (1974).
Dalton et al., Aust. J. Chem., 25, 625-32 (1972).

Primary Examiner—John M. Ford
Attorney, Agent, or Firm—Charles M. Kinzig; Janice E. Williams; Alan D. Lourie

[57] ABSTRACT

The invention relates to thiadiazinone derivatives that have utility as cardiac stimulants. A compound of the invention is 7-(1H-imidazol-1-yl)-9,9a-dihydroindeno[1,2-e][1,3,4]-thiadiazin-2(3H)-one.

12 Claims, No Drawings

HETEROCYCLIC COMPOUNDS

This application is a continuation-in-part of U.S. patent applicaion No. 041,819, filed Apr. 23, 1987, now abandoned.

The present invention relates to heterocyclic compounds and in particular to such compounds having a thiadiazinone ring as part of a tricyclic structure. This invention further relates to pharmaceutical compositions containing them and a method of stimulating cardiac activity by administering them. The compounds of this invention are phosphodiesterase type III inhibitors and are of use in combatting such conditions wherein such inhibition is thought to be beneficial. Thus the compounds of this invention are positive inotropic agents and vasodilators and are therefore of value in combatting cardiovascular disease, in particular congestive heart failure. In addition the compounds of this invention inhibit platelet aggregation and therefore have an antithrombotic effect. Furthermore the compounds of this invention are bronchodilators and are therefore of use in combatting chronic obstructive lung diseases such as asthma and bronchitis. The compounds of this invention are also anti-arrhythmic agents and are therefore useful in combatting cardiac arrhythmias. The major utility of the compounds of this invention is in the treatment of congestive heart failure, for such treatment the compounds have a very desirable profile of activity.

Accordingly the present invention provides compounds of the formula (1):

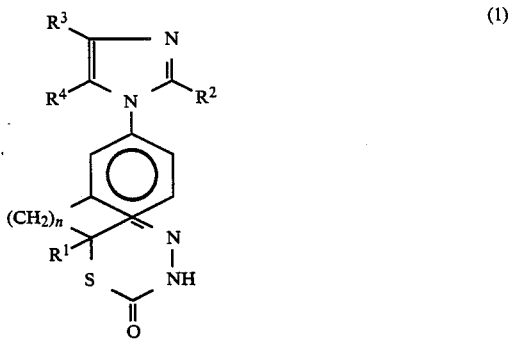

and pharmaceutically acceptable salts thereof, wherein:
$R^1$ is hydrogen or methyl;
n is one, and when $R^1$ is hydrogen n can also be two;
$R^2$, $R^3$ and $R^4$ are independently hydrogen, $C_{1-4}$alkyl or hydroxy($C_{1-4}$)alkyl.

Suitably $R^1$ is hydrogen. Suitably $R^1$ is methyl.

Examples of $C_{1-4}$alkyl for $R^2$, $R^3$ and $R^4$ are methyl, ethyl, propyl and butyl. Examples of hydroxy($C_{1-4}$)alkyl for $R^2$, $R^3$ and $R^4$ are hydroxymethyl, and 2-hydroxyethyl.

In a favoured aspect n is one thus forming a dihydroindenothiadiazinone ring system. In an alternative aspect n is two thus forming a dihydronaphthothiadiazinone ring system.

Specific componds of this invention include:
7-(1H-imidazol-1-yl)-9,9a-dihydroindeno[1,2-e][1,3,4]-thiadiazin-2(3H)-one,
7-(1H-imidazol-1-yl)-9a-methyl-9,9a-dihydroindeno[1,2-e][1,3,4]-thiadiazin-2(3H)-one,
7-(1H-imidazol-1-yl)-9,10-dihydro-10aH-naphtho[1,2-e][1,3,4]-thiadiazin-2(3H)-one,
7-(2-methyl-1H-imidazol-1-yl)-9,9a-dihydroindeno[1,2-e][1,3,4]thiadiazin-2(3H)-one,
7-(4-methyl-1H-imidazol-1-yl)-9,9a-dihydroindeno[1,2-e][1,3,4]thiadiazin-2(3H)-one,
7-(2-ethyl-4-methyl-1H-imidazol-1-yl)-9,9a-dihydroindeno[1,2-e][1,3,4]thiadiazin-2(3H)-one,
7-(2,4-dimethyl-1H-imidazol-1-yl)-9,9a-dihydroindeno[1,2-e][1,3,4]thiadiazin-2(3H)-one, and
7-(4-hydroxymethyl-1H-imidazol-1-yl)-9,9a-dihydroindeno[1,2-e][1,3,4]thiadiazin-2(3H)-one,
and pharmaceutically acceptable salts thereof.

This invention covers all tautomeric forms of the compounds of the formula (1) and all optical isomeric forms thereof.

Compounds of the formula (1) may form pharmaceutically acceptable acid-addition salts with either organic or inorganic acids, for example those formed with hydrochloric, hydrobromic, hydriodic, methanesulphonic, sulphuric, maleic, fumaric, succinic, acetic, oxalic, tartaric, citric and lactic acids.

In order to use a compound of the formula (1) or a pharmaceutically acceptable acid salt thereof for the treatment of mammals including humans it is normally formulated in accordance with standard pharmaceutical practice as a pharmaceutical composition.

Compounds of formula (1) and their pharmaceutically acceptable salts may be administered in standard manner for the treatment of the indicated diseases, for example orally, parenterally, trans-dermally, rectally, via inhalation of via buccal administration. Preferably the compounds of formula (1) and their pharmaceutically acceptable salts are administered parenterally.

Compounds of formula (1) and their pharmaceutically acceptable salts which are active when given orally or via buccal administration can be formulated as syrups, tablets, capsules and lozenges. A syrup formulation will generally consist of a suspension or solution of the compound or salt in a liquid carrier for example, ethanol, glycerine or water with a flavouring or colouring agent. Where the composition is in the form of a tablet, any pharmaceutical carrier routinely used for preparing solid formulations may be used. Examples of such carriers include magnesium stearate, starch, lactose and sucrose. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be considered, for example aqueous gums, celluloses, silicates or oils and are incorporated in a soft gelatin capsule shell.

Typical parenteral compositions consist of a solution or suspension of the compound or salt in a sterile aqueous or non-aqueous carrier optionally containing a parenterally acceptable oil, for example polyethylene glycol, polyvinylpyrrolidone, lecithin, arachis oil, or sesame oil.

A typical suppository formulation comprises a compound of formula (1) or a pharmaceutically acceptable salt thereof which is active when administered in this way, with a binding and/or lubricating agent, for example polymeric glycols, gletains, cocoa-butter or other low melting vegetable waxes or fats.

Typical transdermal formulations comprise of a conventional aqueous or non-aqueous vehicle, for example a cream, ointment, lotion or paste or in the form of a medicated plaster, patch or membrane.

Typical compositions for inhalation are in the form of a solution, suspension or emulsion that may be administered in the form of an aerosol using a conventional propellant such as dichlorodifluoromethane or trichlorofluoromethane.

Preferably the composition is in unit dosage form, for example an ampoule, vial, pre-filled syringe, tablet, capsule or metered aerosol dose.

Each dosage unit for oral administration contains suitably from 0.01 mg/Kg to 3 mg/Kg, and preferably from 0.05 mg/Kg to 1.5 mg/Kg, and each dosage unit for parenteral administration contains suitably from 0.001 mg/Kg to 1 mg/Kg, of a compound of formula (1) or a pharmaceutically acceptable salt thereof calculated as the free base.

The daily dosage regimen for oral administration is suitably about 0.01 mg/Kg to 12 mg/Kg, of a compound of formula (1) or a pharmaceutically acceptable salt thereof calculated as the free base. The daily dosage regimen for parenteral administration is suitably about 0.001 mg/Kg to 4 mg/Kg, for example about 0.01 mg/Kg to 1 mg/Kg, of a compound of the formula (1) or a pharmaceutically acceptable salt thereof calculated as the free base. The active ingredient may be administered as required, for example from 1 to 8 times a day or by infusion, sufficient to increase cardiac output. The compositions of the present invention have positive inotropic activity and vasodilator activity and are of use in the treatment of cardiovascular diseases which can be treated by compounds having either or both of these activities. One such disease condition is congestive heart failure. The compounds of the formula (1) wherein $R^2$, $R^3$ and $R^4$ are not all hydrogen are likely to be particularly useful in view of their selective action, e.g. by virtue of their weak inhibition of cytochrome P450 enzyme systems. The compounds of the invention are also bronchodilators and are useful in chronic obstructive lung disease for example asthma and bronchitis. The compositions of this invention are also anti-arrhythmic agents and are useful in treating and preventing cardiac arrhythmias. Such conditions can be treated by administration orally, rectally, parenterally or by inhalation. For administration by inhalation dosages are controlled by a valve, are administered as required and for an adult are conveniently in the range 0.1–5.0 mg of a compound of the formula (1) or a pharmaceutically acceptable salt thereof.

The compounds of this invention may be co-administered with other pharmaceutically active compounds, for example in combination, concurrently or sequentially. Conveniently the compounds of this invention and the other active compound or compounds are formulated in a pharmaceutical composition. Examples of compounds which may be included in pharmaceutical compositions with the compounds of the formula (1) are vasodilators for example hydralazine, angiotensin converting enzyme inhibitors for example captopril, anti-anginal agents for example isosorbide nitrate, glyceryl trinitrate and pentaerythritol tetranitrate, anti-arrhythmic agents for example quinidine, procainamide and lignocaine, cardioglycosides for example digoxin and digitoxin, calcium antagonists for example verapamil and nifedipine, diuretics such as thiazides and related compounds for example bendrofluazide, chlorothiazide, chlorothalidone, hydrochlorothiazide, and other diuretics for example frusemide and triamterene, and sedatives for example nitrazepam, flurazepam and diazepam.

The compounds of the formula (1) or pharmaceutically acceptable salts thereof may be prepared by a process which comprises:

(a) for preparing a compound of the formula (1) wherein $R^1$ is hydrogen, reacting a compound of the formula (2):

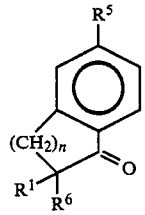

(2)

wherein $R^1$ is hydrogen, $R^5$ is a group (A):

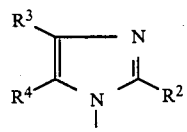

(A)

or a precursor thereof, $R^6$ is halo, and n, $R^2$, $R^3$ and $R^4$ are as hereinbefore defined, with a compound of the formula (3):

$R^7OCSNHNH_2$  (3)

wherein $R^7$ is $C_{1-4}$alkyl; or (b) cyclizing a compound of the formula (4):

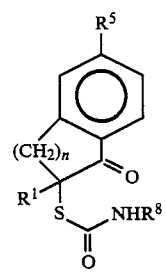

(4)

wherein $R^1$ is hydrogen or methyl and $R^5$ and n are as hereinbefore defined, and $R^8$ is optionally protected amino, in the presence of acid;

and thereafter if necessary:

(i) converting a group $R^5$ to a group (A) as hereinbefore defined, (ii) removing any protecting group, (iii) forming a pharmaceutically acceptable salt.

Suitably the reaction of the compounds of the formulae (2) and (3) is performed in an organic solvent for example a $C_{1-4}$alkanol such as ethanol, or in acetonitrile. The reaction is conveniently performed at an elevated temperature for example under reflux conditions. Suitably $R^6$ is bromo or chloro, preferably bromo. Suitably $R^7$ is methyl.

Suitably the cyclization of a compound of the formula (4) is performed in an aqueous inorganic acid, for example hydrochloric acid, or in an organic solvent containing an aqueous inorganic acid, for example in dimethylformamide or a $C_{1-6}$alkanol, such as ethanol in admixture with hydrochloric acid. The cyclization is conveniently performed at an elevated temperature for example 60° C. to 140° C., preferably at reflux temperature for convenience.

The cyclization may be performed on a compound of the formula (4) wherein $R^8$ is amino, or a protected variant of the compound of the formula (4), for example protected on the hydrazine function by an acid-labile protecting group for example isopropylidene or benzylidene i.e. $R^8$ is $-N{=}C(CH_3)_2$ or $-N{=}CHC_6H_5$.

An example of $R^5$ being a precursor to a group (A) as hereinbefore defined is when $R^5$ is a halo group, preferably fluoro, which may react with a compound of the formula (5):

 (5)

wherein $R^2$, $R^3$ and $R^4$ are as hereinbefore defined, at an elevated temperature in the absence of a solvent or in an organic solvent such as dimethylsulphoxide, dimethylformamide or N-methyl-pyrrolidone optionally in the presence of a base such as an alkali metal carbonate.

Pharmaceutically acceptable salts of the compounds of the formula (1) may be prepared in conventional manner, for example acid addition salts may be prepared by treating the compounds of the formula (1) with the appropriate acid in a $C_{1-4}$alkanol, or they may be prepared by the use of an ion-exchange resin to form the desired salt directly from the free base or via a different acid addition salt.

The compounds of the formula (4) may be conveniently prepared by reacting a compound of the formula (2) wherein $R^1$ is hydrogen or methyl, and $R^5$, $R^6$ and n are as hereinbefore defined, with a compound of the formula (6):

$$M^{\oplus\ominus}O-CS-NHR^8 \qquad (6)$$

wherein $R^8$ is as hereinbefore defined and $M^+$ is a counter-ion, for example an alkali metal ion such as potassium or sodium or an ammonium ion.

Suitably the reaction of the compounds of the formulae (2) and (6) is performed in an organic solvent such as a $C_{1-4}$alkanol, dimethylformamide or acetonitrile. The reaction is conveniently performed at a non-extreme temperature for example between −10° C. and 80° C., preferably between 0° and 30° C.

The compound of the formula (4) need not be isolated but may be cyclized in situ in the presence of acid as hereinbefore described.

If it is desired to prepare a protected compound of the formula (4) then the compound of the formula (6) may be in protected form, for example as the isopropylidene. In an alternative the compound of the formula (4) may be protected, if desired, after the reaction of the compounds of the formulae (2) and (6).

The compounds of the formula (2) may be conveniently prepared by halogenating a compound of the formula (7):

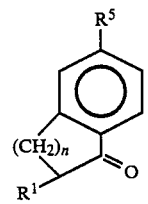 (7)

wherein $R^1$ is hydrogen or methyl, and $R^5$ and n are as hereinbefore defined. Suitably to prepare compounds wherein $R^6$ is bromo, the reaction is performed in a chlorinated organic solvent, for example chloroform with a solution of bromine. The reaction is conveniently performed at a non-extreme temperature such as between −20° and 60° C., preferably between 0° and 30° C. Preferably to prepare compounds wherein $R^5$ is a group (A) as hereinbefore defined and $R^6$ is bromo, the reaction is performed in a solution of bromine and hydrogen bromide in acetic acid at a non-extreme temperature such as between −20° and 80° C., preferably between 30° and 70° C.

The compounds of the formula (7) wherein $R^5$ is a group (A) may be prepared from the compounds of the formula (7) wherein $R^5$ is a precursor to a group (A), such as fluoro, by reaction with a compound of the formula (5) in an analogous manner to that hereinbefore described for the preparation of compounds of the formula (1).

The compounds of the formula (7) wherein $R^5$ is fluoro are known or preparable in conventional manner from U.S. Pat. No. 4616013.

The following biological test methods and Examples serve to illustrate this invention.

Cardiac Stimulant Activity—In vivo (Anaesthetised Cats)

In anaesthetised cats pretreated with a ganglion blocker (pempidine) and propranolol, the compounds of the Examples causes sustained increases in left ventricular dp/dt max (this is an index of left ventricular contractility) when administered intravenously. The dose to increase left ventricular dp/dt max by 50% is given as the $ED_{50}$. The compound of Example 1 gave an $ED_{50}$ (micromol/kg) value of 0.09 and displayed a short duration of activity. In comparison amrinone gave a value of 5.6.

A compound with a rapid onset and short duration of activity is particularly useful for intra venous (i.v.) infusion, for example for acute i.v. use in the treatment of congestive heart failure or status asthmaticus, since i.v. infusion of such a compound has the following advantages:
 (i) the pharmacological effect is rapid when the infusion is commenced,
 (ii) the titration of the dose to suit the individual patient is facilitated, and
 (iii) the pharmacological effect is not sustained when infusion is halted.

Inhibition of Phosphodiesterases

Three peaks of cyclic nucleotide phosphodiesterase activity [PDE (Peak I), PDE (Peak II) and PDE (Peak III)] from cat heart were separated by chromatography on DEAE-Sepharose CL-6B (Diethylaminoethyl Cellulose with a bead size of 45–165 microns). Sepharose is a registered trademark of Pharmacia Fine Chemicals Inc. The high-speed supernatant from a cat heart homogenate (2 g) tissue in 20 ml 20 mM PIPES (Piperazine-N-N'-bis[2-ethanesulfonic acid]), 50 mM Na acetate, pH 6.5) was applied to a 15×1.5 cm column of *DEAE-Sepharose equilibrated with the homogenisation buffer. The PDE activities were eluted with a gradient of 0.05-1M Na acetate in 20 mM PIPES. There were three major peaks which had the following characteristics:

| PDE (Peak I) - eluted at 0.15 M Na acetate | | | |
|---|---|---|---|
| Substrate | 50 μg/ml calmodulin (+ = added) | Km (μM) | Relative $V_{max}$ |
| cyclic AMP | — | 0.5 | 1 |
| cyclic GMP | — | 1.8 | 1.1 |
| cyclic AMP | + | 0.7 | 6.3 |
| cyclic GMP | + | 1.4 | 7.2 |

| PDE (Peak II) - eluted at 0.3 M Na acetate | | |
|---|---|---|
| Substrate | Km (μM) | Relative $V_{max}$ |
| cyclic AMP | 6 | 1 |
| cyclic GMP | 28 | 0.2 |

| PDE (Peak III) - eluted at 0.5 M Na acetate | | |
|---|---|---|
| Substrate | Km (μM) | Relative $V_{max}$ |
| cyclic AMP | 0.6 | 1 |
| cyclic GMP | 2.9 | 0.4 |

PDE (Peak I) has high affinity for cyclic AMP and cyclic GMP and is characterised by an activation by $Ca^{2+}$/calmodulin complex.

PDE (Peak II) demonstrates relatively low affinities for both cyclic AMP and cyclic GMP and is not affected by $Ca^{2+}$/calmodulin complex.

PDE (Peak III) has high affinity for cyclic AMP. It can also hydrolyse cyclic GMP through the preferred substrate is cyclic AMP. This activity is also insensitive to $Ca^{2+}$/calmodulin activation.

Enzyme assay

The enzyme was assayed by incubation at 37° for 4-30 min in 50 mM Tris, 5 mM $MgCl_2$, pH 7.5 with [3-H] cyclic nucleotide ($4\times10^5$ disintegrations $min^{-1}$) and [14-C] nucleotide 5' monophosphate ($3\times10^3$ disintegrations $min^{-1}$). The assay was stopped by boiling, and the [3-H] 5'monophosphate product separated from substrate on boronate columns (Davis, C. W. and Daly, J. W. (1979) J. Cyclic Nucleotide Res., 5, 65-74). The reaction mixture was diluted with 0.5 ml 100 mM HEPES (N-2-Hydroxyethylpiperazine-N'-2-ethanesulfonic acid), 100 mM NaCl, pH 8.5, and applied to the column. The column was extensively washed with the same buffer, and the 5' nucleotide eluted with 6 ml 0.25M acetic acid. The recovery of product as judged by [14-C] recovery was approximately 80%. All assays were linear with time of incubation and concentration of enzyme over the range used in these experiments.

Calculation of $IC_{50}$ values $IC_{50}$ values (the concentration of inhibitor required for 50% inhibition of activity) were obtained for PDE (Peak III) by incubation of the enzyme at 1 μM cyclic AMP, and a range of inhibitor concentrations from $0.1\times IC_{50}$ to $100\times IC_{50}$.

| Compound of Example | $IC_{50}\times 10^{-6}$ M |
|---|---|
| 1 | 0.54 |
| Amrinone | 51.8 |
| Milrinone | 2.2 |

EXAMPLE 1

7-(1H-Imidazol-1-yl)-9,9a-dihydroindeno[1,2-e][1,3,4]thiadiazin-2(3H)-one (a) A stirred melt of 5-fluoro-1-indanone (15 g) and imidazole (30 g) was heated at 160°-170° C. for 2 hours under nitrogen. The melt was allowed to cool to about 80° C. then it was digested with hot ethyl acetate (500 ml) and the filtered digest was cooled, washed with water, and extracted with dilute hydrochloric acid. The extract was washed with dichloromethane, then treated with potassium carbonate to pH 8 to give a crude product, 8.78 g. Recrystallisation from water gave a solid 6.34 g, m.p. 147.5°-149° C. which was recrystallised from toluene to give 5-(1H-imidazol-1-yl)-1-indanone, m.p. 148°-150° C., in 78% recovery.

(b) Bromine (0.54 ml) was added dropwise to a stirred solution of 5-(1H-imidazol-1-yl)-1-indanone (2 g) in acetic acid (20 ml) containing hydrogen bromide (1.82 ml of a 45% w/v solution in acetic acid) at 70° C. After 30 minutes the solution was added to cold water (100 ml) and the solution was cooled in ince while potassium carbonate was added to pH 6. The aqueous solution was decanted from a gum, extracted with dichloromethane (60 ml), the extract combined with the gum and the resultant solution was washed with brine, dried over sodium sulphate, and evaporated under reduced pressure at room temperature to a volume of 10-20 ml. This solution contained 2-bromo-5-(1H-imidazol-1-yl)-1-indanone.

To the above solution was added potassium thiocarbazate (1.95 g), potassium bicarbonate (1 g) and dry dimethylformamide (DMF) (20 ml). Residual dichloromethane was removed by evaporation on a rotary evaporator under reduced pressure at 30° C. to leave a suspension in DMF, which was rotated at 30° C. for a further one hour. Water (80 ml) was then added, followed by concentrated hydrochloric acid to pH 2. The solution was heated on a steam bath for 5 minutes, then cooled and potassium bicarbonate was added to pH 7-8 to give a crude product, 1.93 g, m.p. 220° C. dec. Recrystallisation from aqueous ethanol afforded the pure title compound, 1.1 g, m.p. 235°-237° C. dec.

EXAMPLE 2

7-(1H-Imidazol-1yl)-9,9a-dihydroindeno[1,2-e][1,3,4]thiadiazin-2(3H)-one

Bromine (0.14 ml) in a little acetic acid was added to a stirred solution of 5-(1H-imidazol-1-yl)-1-indanone (0.5 g) in acetic acid (5 ml) containing hydrogen bromide (0.48 ml of a 45% w/v solution in acetic acid) at 70° C.

After 30 minutes the mixture was allowed to cool and methoxythiocarbonylhydrazine (0.4 g) was added and the stirred mixture was heated under reflux for 1 hour. Evaporation left a gum which was dissolved in water (25 ml) and sodium bicarbonate was added to pH 6-7 to give a crude product, 0.55 g, m.p. 160°-185° C. dec, thin layer chromatography analysis of which indicated the presence of the same product as obtained in Example 1(b) above.

EXAMPLE 3

7-(1H-Imidazol-1-yl)-9a-methyl-9,9a-dihydroindeno[1,2-e][1,3,4]thiadiazin-2(3H)-one (a) A stirred melt of 5-fluoro-2-methyl-1-indanone (4.9 g) and imidazole (9.8 g) was heated under nitrogen at 175° C. for 2 hours. The warm melt was diluted with ethyl acetate (100 ml), the resulting solution extracted with dilute hydrochloric acid, and the acidic extract treated with potassium carbonate to pH 6. Extraction of the mixture with ethyl acetate with dichloromethane failed to dissolve all of the solids and the mixture was filtered to remove a solid by-product, 5-(1H-imidazol-1-yl)-2-methyl-1H-inden-1-one, 0.92 g, m.p. 215°–217° C. (from toluene). The combined aqueous and organic solutions were evaporated to leave an aqueous mixture which deposited a sticky solid; further product was obtained by ethyl acetate extraction. The combined crude product (5.36 g) was purified by medium pressure column chromatography (silica gel, chloroform) to give 5-(1H-imidazol-1-yl)-2-methyl-1-indanone, 3 g (47%), m.p. 103°–106° C., which was used directly in the next stage.

(b) Following a procedure similar to that of Example 1(b), 5-(1H-imidazol-1-yl)-2-methyl-1-indanone (0.75 g) gave the crude title compound, 0.68 g. Re-precipitation of this solid from water (made acidic (pH 2) with 2 Normal HCl) by the addition of 2 Normal $NH_4OH$ to ca pH 6 gave the title compound, 0.56 g (56%), m.p. ca 253°–255° C. dec. $\delta$(DMSO-$d_6$): 1.53 (3H, s); 3.24 (2H, s); 7.17 (1H, s), 7.7–7.86 (4H, m) and 8.38 (1H, s); 11.7 (1H, s).

EXAMPLE 4

7-(2-Methyl-1H-imidazol-1-yl)-9,9a-dihydroindeno[1,2-e][1,3,4]thiadiazine-2-(3H)-one In a similar manner to Example 1a reaction of 2-methyl-imidazole (13.1 g) with 5-fluoro-1-indanone (6 g) afforded after recrystallization from toluene 5-(2-methyl-1H-imidazol-1-yl)-1-indanone, 1.92 g, m.p. 172°–173° C. 5-(2-Methyl-1H-imidazol-1-yl)-1-indanone (1.8 g) was converted in analogous manner to Example 1b to the title compound, 1.22 g, m.p. >220° C. (recrystallised from aqueous n-propanol), $\delta$(DMSO-$d_6$): 2.3 (3H, s); 3.05, 3.67 (2H, 2×dd), 4.69 (1H, dd), 6.94, 7.34 (2H, 2×s), 7.5 (1H, d), 7.5 (1H, s), 7.8 (1H, d), 11.7 (1H, s).

EXAMPLE 5

7-(4-Methyl-1H-imidazol-1-yl)-9,9a-dihydroindeno[1,2-e][1,3,4]thiadiazine-2-(3H)-one In a similar manner to Example 1a reaction of 4-methyl-imidazole (13.1 g) with 5-fluoro-1-indanone (6 g) afforded after recrystallisation from water and then toluene 5-(4-methyl-1H-imidazol-1-yl)-1-indanone, 1.67 g, m.p. 138°–140° C. 5-(4-Methyl-1H-imidazol-1-yl)-1-indanone (1.57 g) was converted in analogous manner to Example 1b to the title compound, 0.9 g, m.p. >220° C. (recrystallised from aqueous n-propanol), $\delta$(DMSO-$d_6$): 2.2 (3H, s), 3.04, 3.65 (2H, 2×dd), 4.67 (1H, dd), 7.6–7.8 (4H, m), 8.54 (1H, s), 11.7 (1H, s).

EXAMPLE 6

Substitution of
(a) 2-ethyl-4-methylimidazole,
(b) 2,4-dimethylimidazole,
(c) 4-hydroxymethylimidazole for imidazole in the procedure of Example 1 gives:
(a) 7-(2-ethyl-4-methyl-1H-imidazol-1-yl)-9,9a-dihydroindeno[1,2-e][1,3,4]thiadiazin-2(3H)-one,
(b) 7-(2,4-dimethyl-1H-imidazol-1-yl)-9,9a-dihydroindeno[1,2-e][1,3,4]thiadiazin-2(3H)-one,
(c) 7-(4-hydroxymethyl-1H-imidazol-1-yl)-9,9a-dihydroindeno[1,2-e][1,3,4]thiadiazin-2(3H)-one.

EXAMPLE 7

A pharmaceutical composition for parenteral administration is prepared by dissolving the title compound of Example 1 (0.02 g) in polyethylene glycol 300 (25 ml) with heating. This solution is then diluted with water for injections Ph. Eur. (to 100 ml). The solution is then sterilised by filtration through a 0.22 micron membrane filter and sealed in sterile containers.

Compositions containing the compound of Example 1 (0.04 g) in polyethylene glycol 300 are prepared in analogous manner.

EXAMPLE 8

Pharmaceutical compositions for oral administration are prepared by combining the following:

|  | % w/w | | |
| --- | --- | --- | --- |
| 7-(1H—imidazol-1-yl)-9,9a-dihydroindeno[1,2-e][1,3,4]-thiadiazin-2(3H)-one | 0.5 | 3.0 | 7.14 |
| 2% w/w Soya lecithin in soya bean oil | 90.45 | 88.2 | 84.41 |
| Hydrogenated vegetable shortening and beeswax | 9.05 | 8.8 | 8.45 |

The formulations are then filled into individual soft gelatin capsules.

What is claimed is:

1. A compound of the formula (1):

or a pharmaceutically acceptable salt thereof, wherein:
$R^1$ is hydrogen or methyl;
n is one, and when $R^1$ is hydrogen n can also be two;
$R^2$, $R^3$ and $R^4$ are independently hydrogen, $C_{1-4}$alkyl or hydroxy($C_{1-4}$)alkyl.

2. A compound according to claim 1 wherein n is one.
3. A compound according to claim 1 wherein $R^1$ is hydrogen.
4. A compound according to claim 1 which is:
7-(1H-imidazol-1-yl)-9,9a-dihydroindeno[1,2-e][1,3,4]thiadiazin-2(3H)-one,
7-(1H-imidazol-1-yl)-9a-methyl-9,9a-dihydroindeno[1,2-e][1,3,4]-thiadiazin-2(3H)-one,
7-(1H-imidazol-1-yl)-9,10-dihydro-10aH-naphtho[1,2-e][1,3,4]-thiadiazin-2(3H)-one, 7-(2-methyl-1H-imidazol-1-yl)-9,9a-dihydroindeno[1,2-e][1,3,4]thiadiazin-2(3H)-one, 7-(4-methyl-1H-imidazol-1-yl)-9,9a-dihydroindeno[1,2-e][1,3,4]thiadiazin-2(3H)-one, 7-(2-ethyl-4-methyl-1H-imidazol-1-yl)-9,9a-dihydroindeno[1,2-e][1,3,4]thiadiazin-2(3H)-one, 7-(2,4-dimethyl-1H-imidazol-1-yl)-9,9a-dihydroindeno[1,2-e][1,3,4]thiadiazin-2(3H)-one, or 7-(4-hydroxymethyl-1H-imidazol-1-yl)-9,9a-dihydroindeno[1,2-e][1,3,4]thiadiazin-2(3H)-one, or a pharmaceutically acceptable salt thereof.

5. A pharmaceutical composition for stimulating cardiac activity which comprises a compound according to claim 1 and a pharmaceutically acceptable carrier.

6. A pharmaceutical composition for effecting bronchodilation which comprises a compound according to claim 1 and a pharmaceutically acceptable carrier.

7. A pharmaceutical composition for effecting phosphodiesterase (type III) inhibition which comprises a compound according to claim 1 and a pharmaceutically acceptable carrier.

8. A method for stimulating cardiac activity in a host in need thereof by administration of a non-toxic but effective amount of a compound according to claim 1.

9. A method for effecting bronchodilatation in a host in need thereof by administration of a non-toxic but effective amount of a compound according to claim 1.

10. A method for effecting phosphodiesterase (type III) inhibition in a host in need thereof by administration of a non-toxic but effective amount of a compound according to claim 1.

11. A method for treating congestive heart failure in a host in need thereof by administration of a non-toxic but effective amount of a compound according to claim 1.

12. A compound of the formula (4):

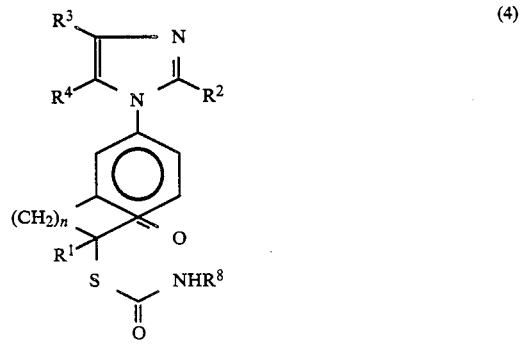

wherein:

$R^1$ is hydrogen or methyl;

n is one, and when $R^1$ is hydrogen n can also be two;

$R^2$, $R^3$ and $R^4$ are independently hydrogen, $C_{1-4}$alkyl or hydroxy($C_{1-4}$)alkyl, and $R^8$ is optionally protected amino.

* * * * *